(12) United States Patent  
Rose, Sr.

(10) Patent No.: US 7,469,783 B2  
(45) Date of Patent: Dec. 30, 2008

(54) PACKAGE FOR PREPASTED BRACKETS

(75) Inventor: Leo P. Rose, Sr., Chesterton, IN (US)

(73) Assignee: TP Orthodontics, Inc., Westville, IN (US)

( * ) Notice: Subject to any disclaimer, the term of this patent is extended or adjusted under 35 U.S.C. 154(b) by 125 days.

(21) Appl. No.: 11/607,595

(22) Filed: Nov. 30, 2006

(65) Prior Publication Data

US 2008/0128297 A1    Jun. 5, 2008

(51) Int. Cl.  
*A61B 19/02* (2006.01)

(52) U.S. Cl. .................. 206/63.5; 206/460; 206/461; 433/9

(58) Field of Classification Search ............. 206/63.5, 206/460, 368, 369, 461, 467, 468, 471; 433/9  
See application file for complete search history.

(56) References Cited

U.S. PATENT DOCUMENTS

| | | | |
|---|---|---|---|
| 4,204,325 A | 5/1980 | Kaelble | |
| 4,948,367 A | 8/1990 | Haas | |
| 4,978,007 A | 12/1990 | Jacobs et al. | |
| 5,172,809 A | 12/1992 | Jacobs et al. | |
| 5,183,403 A | 2/1993 | Masuhara et al. | |
| 5,221,202 A | 6/1993 | James | |
| 5,328,363 A | 7/1994 | Chester et al. | |
| 5,348,154 A | 9/1994 | Jacobs et al. | |
| 5,354,199 A | 10/1994 | Jacobs et al. | |
| 5,429,229 A | 7/1995 | Chester et al. | |
| 5,538,129 A | 7/1996 | Chester et al. | |
| 5,575,645 A | 11/1996 | Jacobs et al. | |
| 5,636,736 A | 6/1997 | Jacobs et al. | |
| 5,759,028 A | 6/1998 | Bozman | |
| 5,762,192 A | 6/1998 | Jacobs et al. | |
| 5,827,058 A | 10/1998 | Kelly et al. | |
| 6,089,861 A | 7/2000 | Kelly et al. | |
| 6,183,249 B1* | 2/2001 | Brennan et al. | 433/9 |
| 6,482,003 B2 | 11/2002 | Dixon et al. | |
| 6,786,720 B1 | 9/2004 | Kesling | |
| 6,834,761 B1 | 12/2004 | Kesling | |
| 6,843,370 B2 | 1/2005 | Tuneberg | |
| 2005/0241962 A1* | 11/2005 | Tuneberg | 206/63.5 |

OTHER PUBLICATIONS

Journal of Clinical Orthodontics, Jul. 2006, vol. XL, No. 7, cover page, pp. 396-397.

* cited by examiner

*Primary Examiner*—David T Fidei  
(74) *Attorney, Agent, or Firm*—Lloyd L. Zickert

(57) ABSTRACT

This invention is in a package and method of packaging ready mountable or prepasted bondable dental appliances, and particularly orthodontic brackets, wherein the appliances include a body and a base, and a layer of uncured polymer resin is applied to the base. The package includes a carrier for the bondable appliances for single or multiple appliances and enclosed in a hermetically sealed bag.

22 Claims, 8 Drawing Sheets

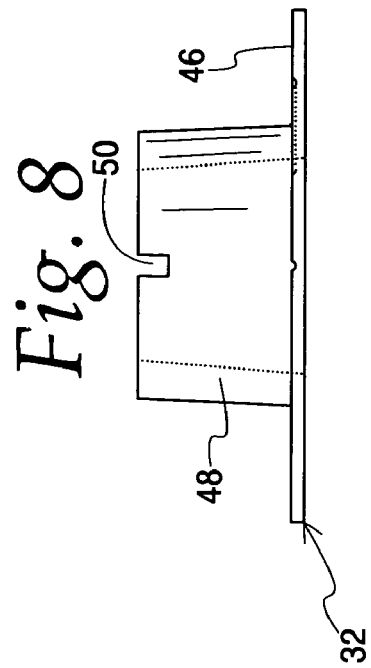
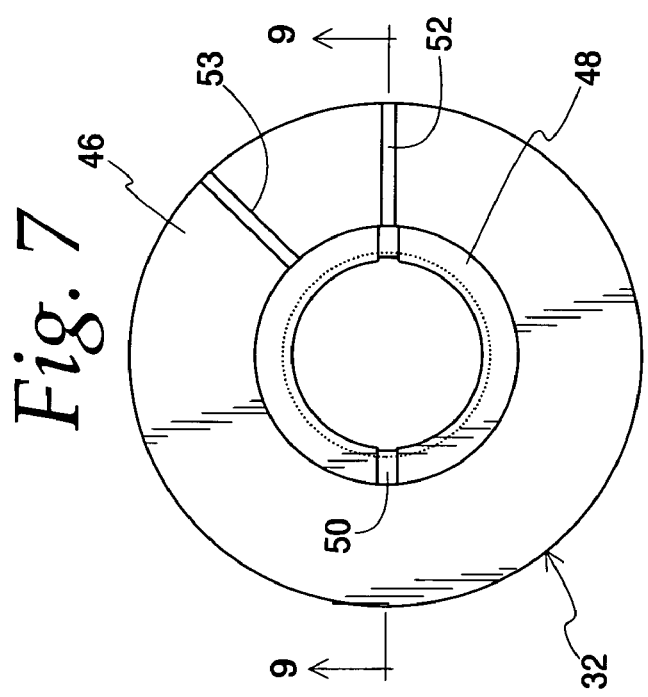
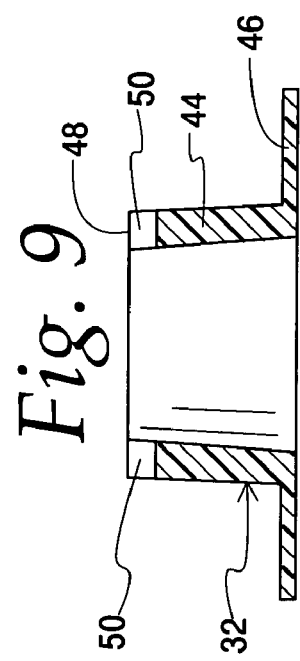

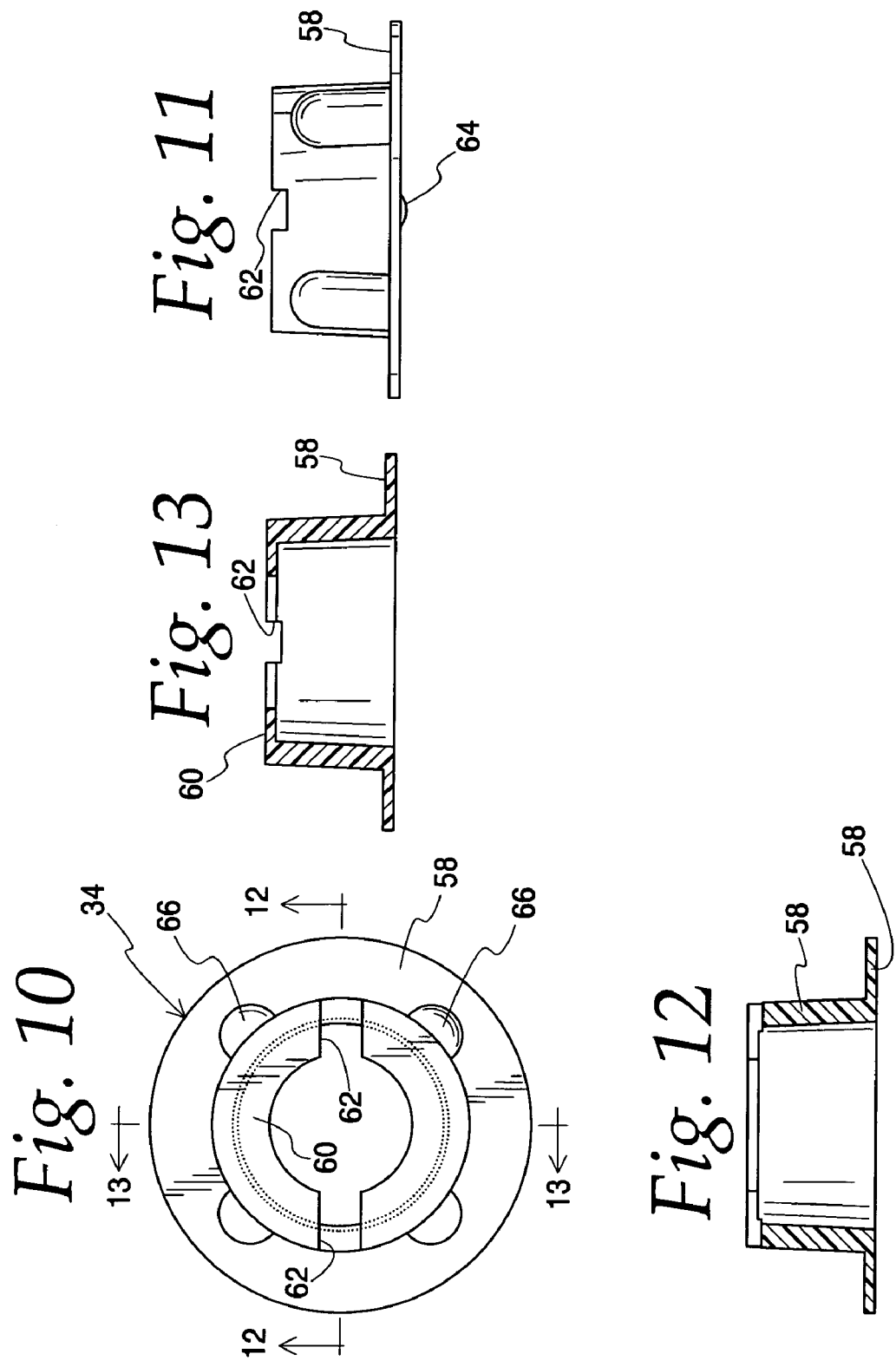

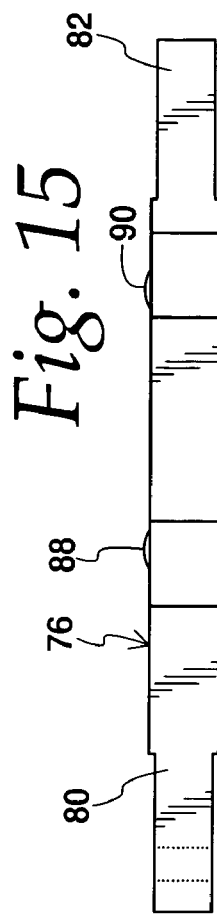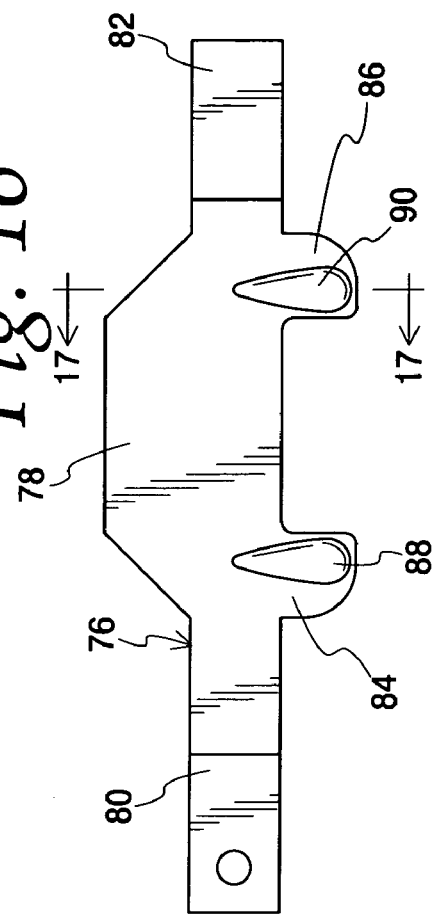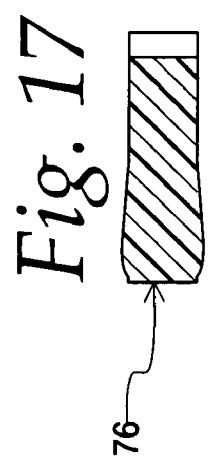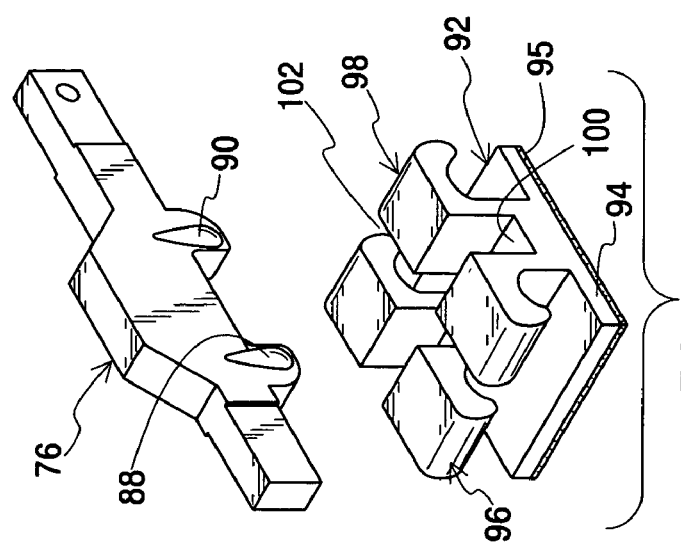

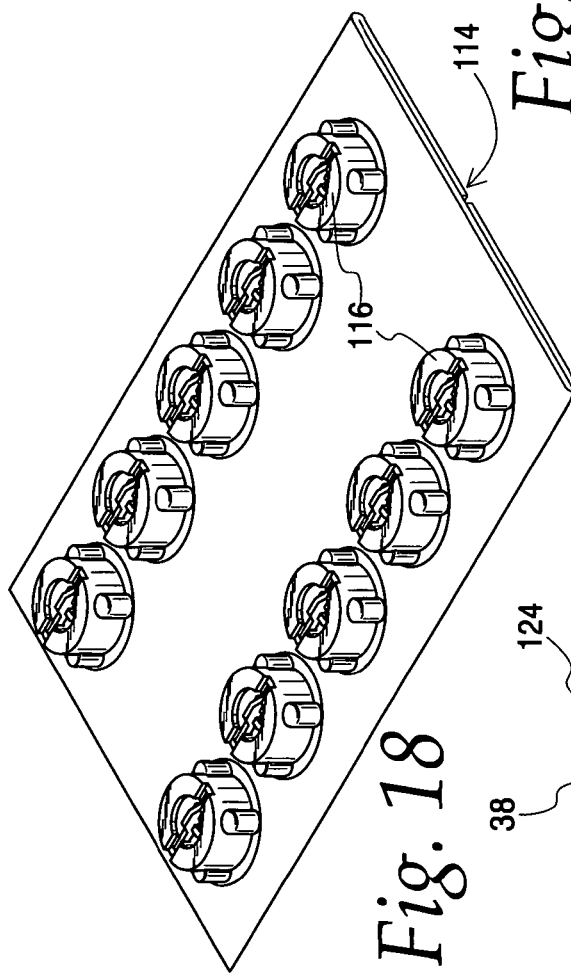
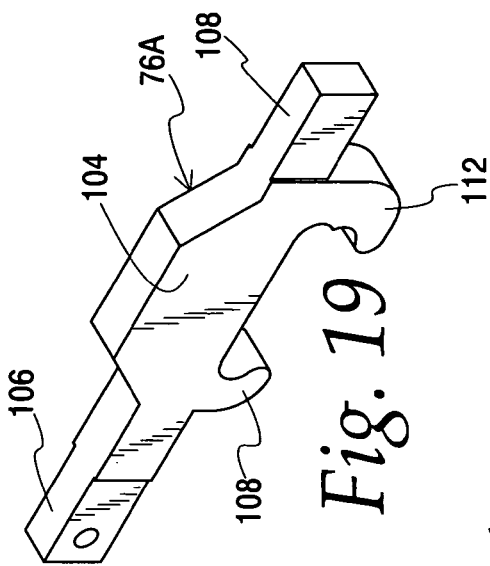
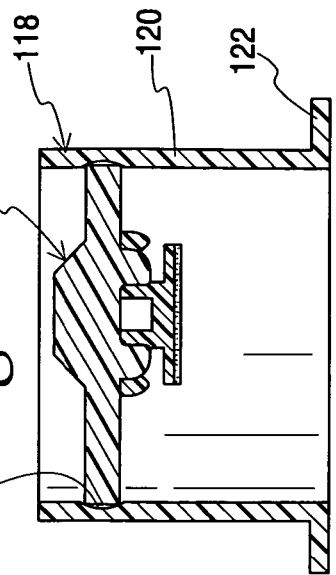
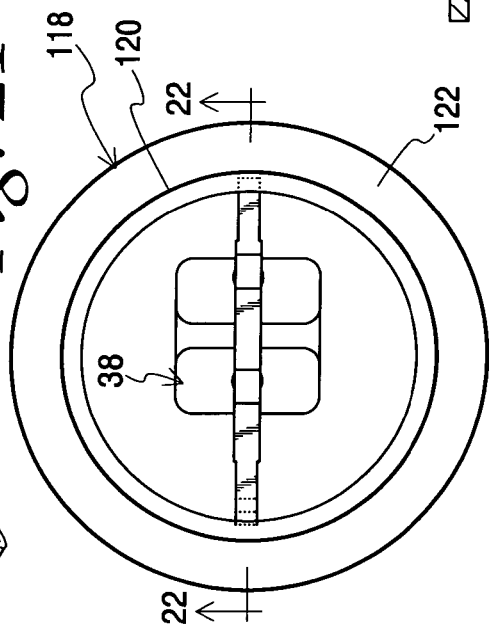
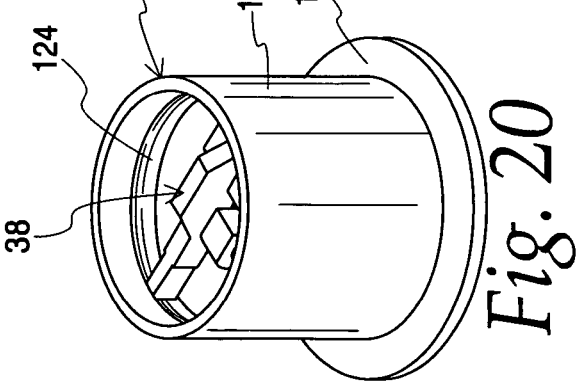

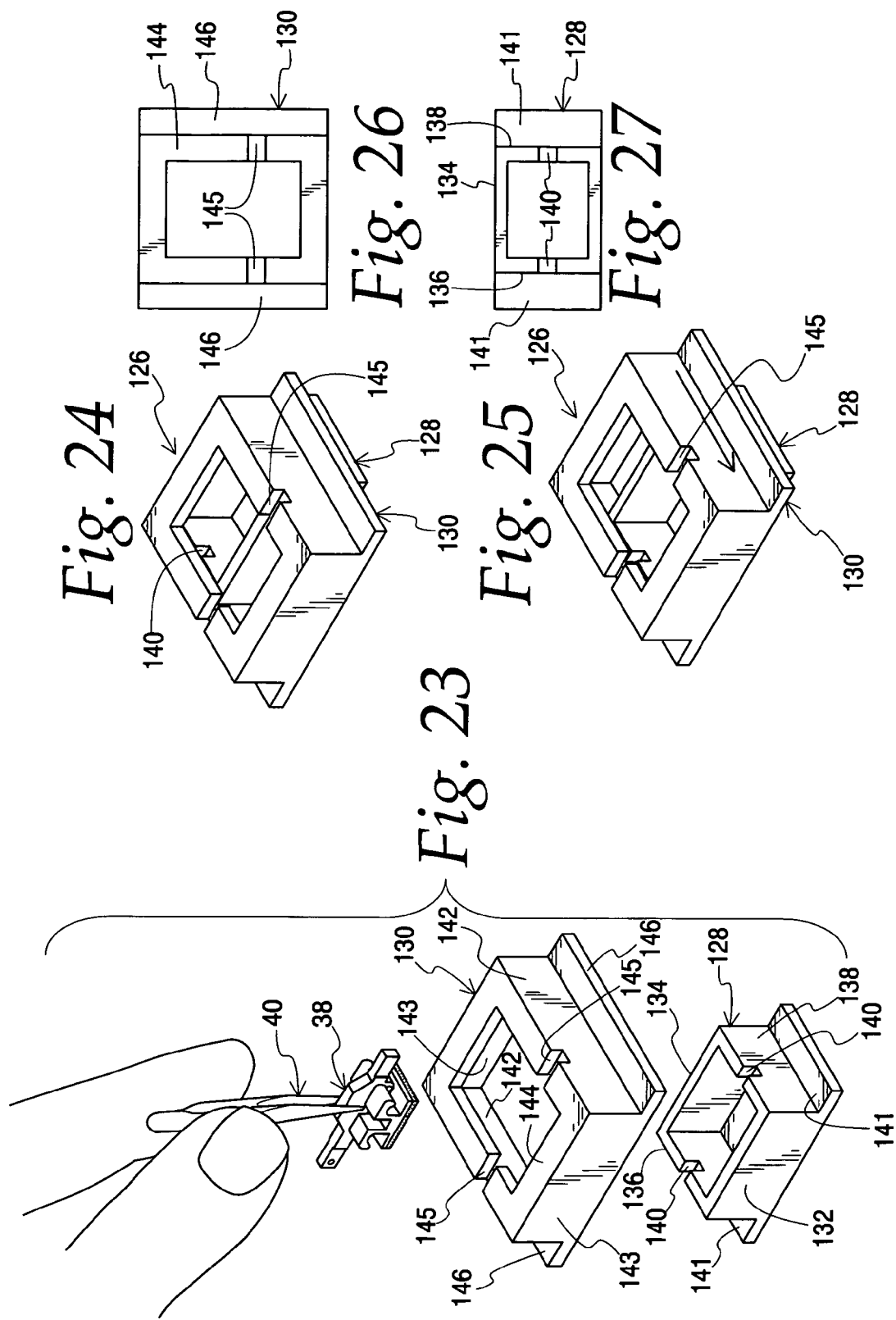

PACKAGE FOR PREPASTED BRACKETS

This invention relates in general to the packaging of orthodontic appliances having bases with uncured bonding material, and more particularly to a carrier for a prepasted orthodontic appliances enclosed in a bag for shipment to and use by a dentist providing orthodontic treatment to patients.

BACKGROUND OF THE INVENTION

Heretofore it has been well known to package prepasted orthodontic appliances for shipment to orthodontic practitioners and allowing the practitioner to directly apply the appliance to a tooth of a person and cure the bondable material. Such packaging of prepasted brackets is shown in U.S. Pat. Nos. 4,978,007; 5,172,809; 5,328,363; 5,348,154; 5,354,199; 5,429,229; 5,538,129; 5,575,645; 5,636,736; 5,762,192; 5,827,058; 6,089,861; and 6,834,761. Appliances disclosed in these patents generally include a metallic or ceramic appliance with a base on which a coating of light-curable adhesive is applied and are placed in individually pocketed trays for shipping.

It has also been well known to provide ready mountable orthodontic appliances having a coating of pressure-sensitive adhesive on their base which is protected during shipping with a releasable backing, as in U.S. Pat. Nos. 4,204,325 and 4,948,367.

Further, it has been known to mount jigs on prepasted brackets and package them in containers having wells for shipment to users, as in U.S. Pat. Nos. 4,978,007; 5,172,809; 5,348,154; and 5,636,736.

It is further known to enclose a carrier for prepasted brackets in a hermetically sealed light-opaque bag, as in U.S. Pat. No. 6,834,761.

SUMMARY OF THE INVENTION

The package of the present invention includes a carrier for receiving and retaining a jigged prepasted appliance such as a bracket, and for protecting uncured bonding material on the base of the appliance from engaging the carrier and also against curing during shipment. Preferably, the package protects prepasted orthodontic brackets having an uncured layer of light-curable adhesive on the base although it should be appreciated that the uncured adhesive may be of a type that is chemically or thermally curable and suitable for bonding the appliances to hard surfaces such as teeth. It should also be appreciated that the appliance may be a buccal tube.

A suitable light-curable polymer resin or adhesive may be used such as a Python Light Cure Adhesive sold by TP Orthodontics, Inc. of LaPorte, Ind. Python is a trademark owned by TP Orthodontics, Inc. A suitable activator-curable type of adhesive would be the Python One-Step Adhesive or the Rite-On No Mix Adhesive sold by TP Orthodontics, Inc. Python One Step and Rite-On are trademarks owned by TP Orthodontics, Inc. Reference to a polymer resin or an adhesive in this application is intended to relate to any suitable light, heat or chemically curable adhesive for bonding appliances to teeth.

The carrier of the invention includes a base having upwardly opening seats for receiving opposed ends of a jig that is removably connected to an appliance. A cover member is associated with the base in slidable relation and provided with means in the form of a lip that can selectively overlie the seats to lock a jigged prepasted appliance to the base. Both the base and the cover are provided with flanges that are sandwiched between substrates to retain the cover on the base. The flange of the base is suitably fixed to one substrate, while the flange of the cover is free to move relative to the base flange. The cover includes a lip overlying the upper edge of the base and having slots for coacting with the seats of the base to allow insertion and removal of a jigged appliance and to lock the jigged appliance in place on the carrier.

Preferably, the base and cover are cylindrically or ring shaped and the cover includes a wall positioned exteriorly of the wall of the base. In another embodiment the base is rectangular in form as is the cover wherein the cover is in slidable relation to the base for aligning seats on the base with slots in the cover to permit insertion and withdrawal of the jigged appliance from the carrier and also to lock the jigged appliance to the carrier.

The carrier may be provided in single form or multiple form to respectively support single or multiple jigged appliances.

The carrier is then inserted into a bag of suitable material to prevent exposure of the uncured polymer resin on the base of an appliance to energy that would cause curing of the resin. In the case of an appliance having a light-curable adhesive on the base, the bag would be of any suitable light opaque material to prevent the transmission of actinic radiation that would cause curing of the adhesive. The interior of the bag may be flushed of air before sealing the carrier in the bag, such as described in U.S. Pat. No. 6,834,761, the disclosure of which is incorporated herein by reference.

The bag material may be of any suitable flexible polymeric material, such as polyethylene or polyester, that would be impermeable to ambient air, water vapor and contaminants, and where a light-curable resin is used on the base of the appliance to also be impermeable to a light energy that would cure the resin. The bag may optionally include a reclosable fastener at one end.

It is contemplated that the package of the invention is particularly suitable for packaging twin tie wing brackets for the edgewise technique, although it should be appreciated that single tie wings for the edgewise technique or other brackets may be packaged as prepasted brackets in the carrier of the invention. Further, the brackets may be of metal, ceramic or plastic.

Moreover, it should be appreciated that the carrier of the invention may be used for prepasted buccal tubes, wherein the jig employed would be one capable of supporting a buccal tube in the carrier.

The base and cover are made of any suitable plastic resin material and formed by molding or otherwise. For example, the base may be of a substantially rigid polyethylene or polystyrene plastic that is suitably molded. Further the cover may be of a suitable polyethylene or polystyrene plastic that is vacuum formed. Any suitable plastic material may be used so long as the cover may easily slide on the base for purposes of loading, locking and unlocking a jigged appliance on the carrier. The jig is made of a softer plastic material so that it can be easily removably connected to the bracket. It may be made of a suitable polystyrene or polyethylene plastic. With respect to a twin tie wing bracket which defines an opening between mesiodistally spaced apart tie wings, the jig would be sized so that its central portion can be press-fit into the opening between the tie wings and thereafter be easily removable when the jig has been used to transport the bracket from the carrier to a tooth and in aligning and mounting a bracket on a tooth. It is well known to use jigs on brackets and appliances for assisting in aligning the appliances on a tooth when bonding or connecting the appliance to the tooth.

The package of the present invention including the carrier is user-friendly to the orthodontic practitioner desiring to have prepasted appliances. With respect to a single prepasted appliance on a carrier, it is only necessary for the user to open the bag and remove the carrier with the appliance from the bag, slide the cover to unlock the jigged appliance, and remove the jigged appliance with the uncured adhesive and apply it directly to the tooth of a patient. Any suitable instrument, such as a tweezers, may be employed to grasp the jig and manipulate the appliance. Where a plurality of carriers are provided on a substrate, the entire substrate with the plurality of carriers and appliances is removed or partially removed from the bag so that the jigged appliances may be unlocked and removed from the carrier for positioning on and bonding to the teeth of a patient. It will be appreciated that a light-cure adhesive is tacky and therefore will stick to the surface of a tooth and when adjusted to the proper position a curing light can be applied to the uncured adhesive to cure the adhesive and securely mount the appliance to the tooth.

Another carrier embodiment of the invention for handling and transporting jigged prepasted appliances is an upstanding member having opposing flexible walls with indents to removably receive opposed ends of the jig.

It is therefore an object of the present invention to provide a package for shipment and/or storage of orthodontic appliances having a base with an uncured adhesive and wherein the package will protect the integrity of the uncured adhesive before the appliance is mounted on a tooth.

Another object of the present invention is to provide a user-friendly carrier for a prepasted dental appliance that may be easily operated to first allow mounting and locking a jigged appliance to the carrier and thereafter to allow unlocking and withdrawal of the appliance from the carrier and mounting of the appliance onto the tooth of a patient.

A further object of the present invention is in the provision of a carrier for a jigged prepasted orthodontic appliance including a base and a cover operable to selectively lock and unlock a jigged appliance to the carrier.

A further object of the present invention is to provide a user-friendly package in the form of a carrier and bag to transport jigged orthodontic appliances having an uncured layer of polymer resin to facilitate the mounting of the appliance onto a tooth by an orthodontic practitioner.

Another object of the present invention is a method of packaging a prepasted orthodontic bracket for shipment to an end user which includes connecting a jig to the bracket, inserting and locking the jigged bracket into a unique carrier, inserting the carrier with the jigged bracket onto a bag and sealing the bag.

Other objects, features and advantages of the invention will be apparent from the following detailed disclosure, taken in conjunction with the accompanying sheets of drawings, wherein like reference numerals refer to like parts.

DESCRIPTION OF THE DRAWINGS

FIG. 7 is an enlarged top plan view of the base of the carrier;

FIG. 8 is an enlarged side elevational view of the base and looking toward the side having one of the slots that defines a seat for the jigged appliance;

FIG. 9 is a transverse cross-sectional view taken along line 9-9 of FIG. 7;

FIG. 10 is an enlarged top plan view of the cover of the carrier;

FIG. 11 is an enlarged side elevational view of the cover of FIG. 10;

FIG. 12 is a transverse cross-sectional view taken along line 12-12 of FIG. 10;

FIG. 13 is a vertical sectional view of the cover taken along line 13-13 of FIG. 10;

FIG. 14 is an enlarged perspective exploded view of a bracket and a jig according to the invention;

FIG. 15 is an enlarged top plan view of the jig shown in FIG. 14;

FIG. 16 is an enlarged front elevational view of the jig shown in FIG. 14;

FIG. 17 is an enlarged transverse sectional view taken through line 17-17 of FIG. 16;

FIG. 18 is a perspective view of a panel having multiple carriers for receiving multiple brackets designated for different teeth;

FIG. 19 is an enlarged perspective view of a modified universal jig that may be used for the retention of orthodontic appliances for mounting onto a carrier;

FIG. 20 is an enlarged perspective view of a modified carrier according to the invention for jigged appliances;

FIG. 21 is an enlarged top plan view of the carrier of FIG. 20;

FIG. 22 is a vertical sectional view taken along line 22-22 of FIG. 21;

FIG. 23 is an enlarged exploded view of a modified carrier according to the invention and also showing a jigged bracket ready to be mounted in a carrier;

FIG. 24 is an enlarged perspective view of the carrier of FIG. 23 showing the cover in locked position relative to the base;

FIG. 25 is an enlarged perspective view of the carrier of FIG. 23 showing the cover in unlocked position relative to the base;

FIG. 26 is an enlarged top plan view of the cover of the carrier of FIG. 23; and FIG. 27 is an enlarged top plan view of the base of the carrier of FIG. 23.

DESCRIPTION OF THE INVENTION

The package of the present invention includes a carrier for a jigged bracket capable of supporting the jigged bracket or appliance so that the uncured adhesive on the base does not contact any part of the carrier. The carrier with the jigged bracket may be provided in single form or multiple form depending upon the requirements of the practitioner using the appliances. In shipping of the appliances, the carrier with the jigged bracket is enclosed within a bag so as to preserve the integrity of the uncured adhesive on the appliance where the adhesive is light-curable. The bag is preferably hermetically sealed about the carrier to prevent entry of any contaminants, and the bag material is opaque to actinic radiation where prepasted brackets with light-curable adhesive are shipped. The bag material may be of a suitable flexible film or plastic that would also have a strength to resist normal handling so that it maintains integrity during the process of shipping and handling.

Figure 1:
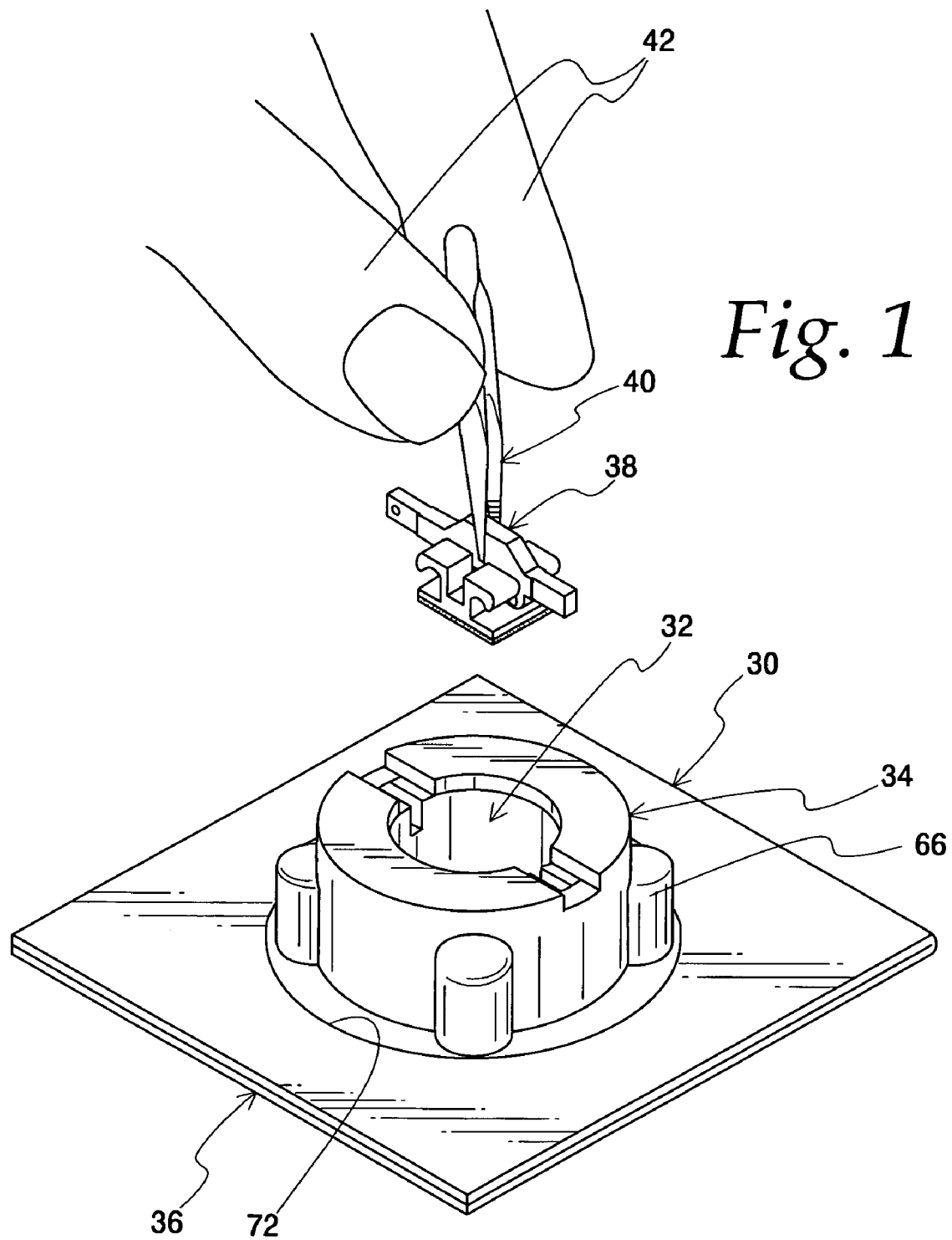
FIG. 1 is an enlarged perspective view of a carrier according to the invention and including a perspective view of a jigged bracket held by a tweezers for insertion into the carrier and also showing the carrier with the cover rotated for loading the jigged bracket onto the carrier.

Referring to FIG. 1, the single appliance carrier, generally indicated by the numeral 30, includes a base 32, a cover 34, and a double thickness panel 36 for retaining the cover on the base and for anchoring the base against rotation, while leaving the cover free to rotate in slidable engagement with the base. A jigged appliance 38 is shown spaced above the carrier and held by a tweezers 40 or other suitable instrument by the fingers 42 of a person. Usually, the jigged appliance is a jigged orthodontic bracket of the edgewise twin-wing type. However, it will be understood that any type of bracket may be supported by a jig for mounting in the carrier. Additionally, a prepasted buccal tube could be supported by the carrier.

Figure 2:
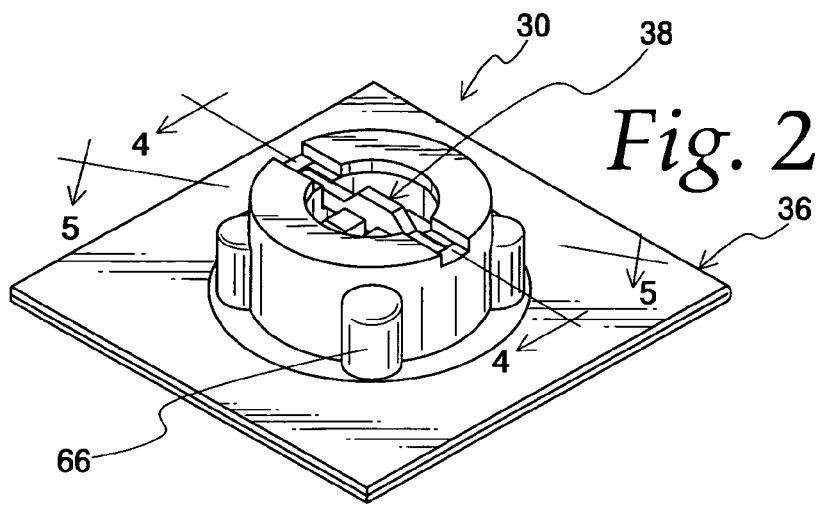
FIG. 2 is an enlarged perspective view of the carrier of FIG. 1 illustrating the jigged bracket in loaded position and the carrier in an unlocked position for insertion or removal of the jigged appliance from the carrier.

A jigged bracket is shown mounted on the carrier 30 in FIG. 2 with the cover positioned to allow loading or unloading of a jigged bracket on the carrier. Thus, the carrier is in unlocked mode. For shipment purposes the cover is rotated as shown in FIG. 3 to lock the jigged appliance in place.

Figure 6:
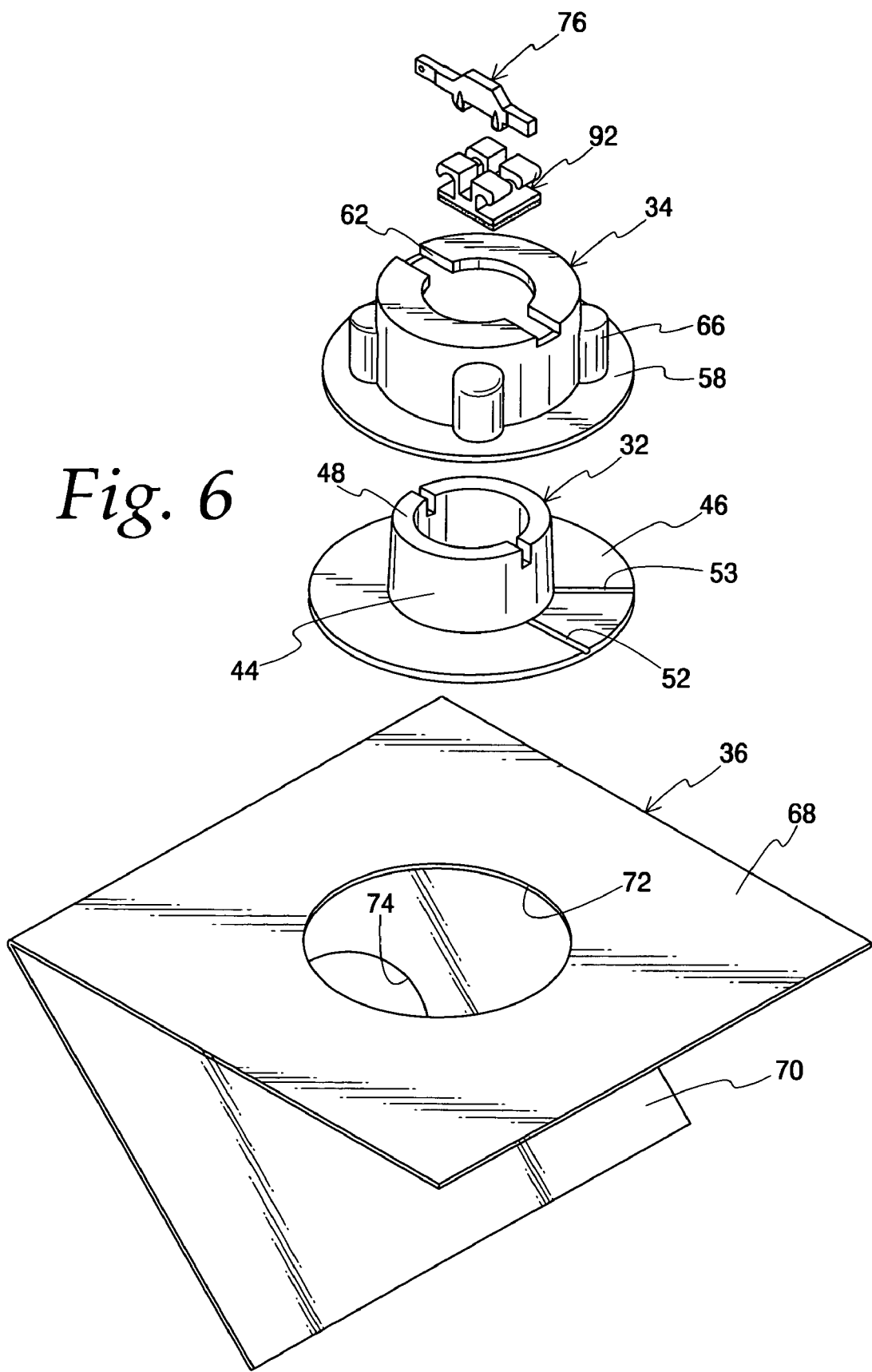
FIG. 6 is an enlarged exploded view of the carrier and also showing an exploded view of a jigged appliance.

Referring to the exploded perspective view of the carrier in FIG. 6, the views of the base in FIGS. 7 to 9, and the views of the cover in FIGS. 10 to 13, the base 32 includes an upstanding generally cylindrical wall 44 having an annularly disposed flange 46 at the lower end of the wall and an upper edge 48 of the wall. The upper edge of the wall is provided with diametrically opposed seats 50 in the form of vertically arranged slots for receiving the ends of a jig removably attached to an orthodontic appliance. While the wall 44 includes slight tapers to facilitate the molding of the base from plastic, it is generally considered to be cylindrical in shape in this embodiment. The base will be suitably molded from a polystyrene plastic although it could be molded from any other type of suitable plastic to render it workable with the cover. The upper sides of the flange 46 may include indents 52 and 53 in the form of shallow recesses for coacting with a detent on the cover to assist in locating the cover relative to the base in unlock or lock positions to allow the jigged appliance to be inserted or loaded on the carrier and removed or withdrawn therefrom, and to lock the jigged appliance to the carrier for handling and shipment.

Referring to FIGS. 10 to 13, the cover 34 includes an upstanding generally cylindrical wall 56 and a peripheral annular flange 58 at the lower end and an inwardly directed locking lip 60 at the upper end. The wall 56 is sized to be slightly larger than the exterior face of the wall 44 of the base so that it will be in suitable sliding engagement with the base and rotatable about the base. The upper lip 60 includes diametrically opposed slots 62 which as seen particularly in FIGS. 2 and 3 may align with the seats 50 of the base to allow insertion and withdrawal of a jigged appliance on the carrier or be offset from the seats to lock the jigged appliance to the carrier. FIG. 2 shows the slots of the cover aligned with the seats with the jigged appliance 38 freely resting in the seats, and FIG. 3 shows the slots offset or misaligned relative to the seats and the jigged appliance 38 locked to the carrier. Similarly, the cover may be made of a polystyrene plastic and it may be vacuum formed or otherwise molded if desired. A detent 64 (FIG. 11) is formed on the underside of the flange 58 for coacting with the indents 52 and 53 (FIG. 7) on the base flange 46 to assist in enabling the user to align the cover slots with the seats of the base and to indicate to the user that the cover has been rotated to a position for locking of a jigged appliance on the carrier. This detent/indent arrangement is optional, although it serves to provide the user a tactile feedback in operating the carrier between locked and unlocked positions. Further, a plurality of ribs 66 are provided on the exterior surface of the upstanding wall 56 of the cover to assist in gripping of the cover for rotating the cover relative to the base. These ribs are optional but can serve to avoid slippage of the fingers on the cover during rotation of the cover relative to the base.

Figure 3:
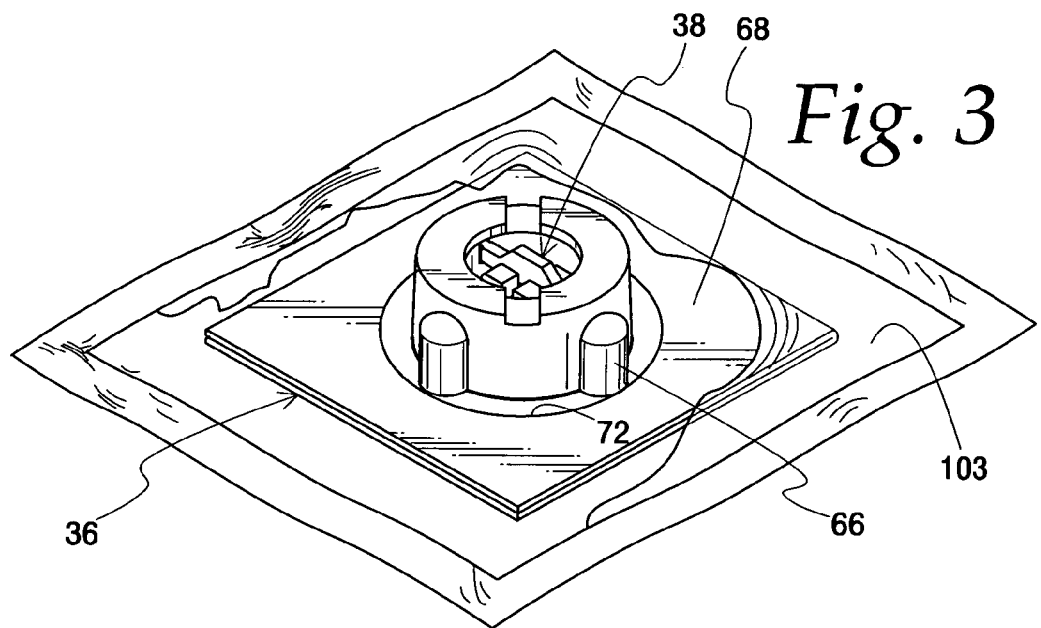
FIG. 3 is an enlarged perspective view of the packaged carrier of FIGS. 1 and 2 in a bag shown in cutaway, and showing the cover of the carrier rotated so that the jigged appliance is locked onto the carrier for shipment.
Figure 4:
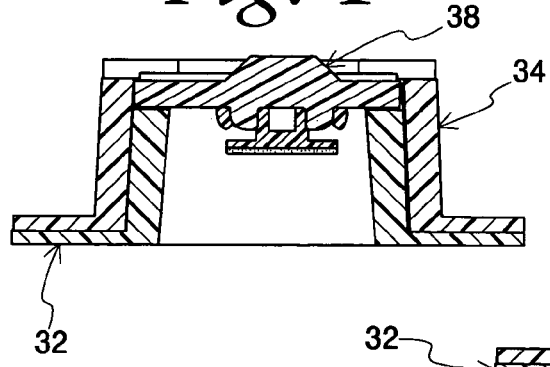
FIG. 4 is a cross section taken generally along line 4-4 of FIG. 2.
Figure 5:
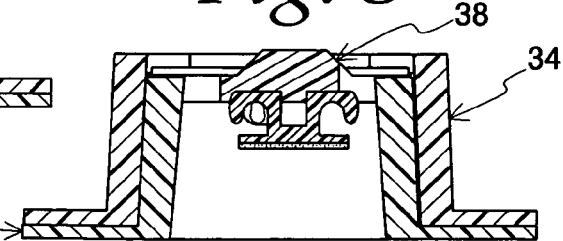
FIG. 5 is a cross section taken generally along line 5-5 of FIG. 2.

Referring now to FIGS. 1, 2, 3 and 6, while any suitable means may be provided to retain the assembled relation of the cover and the base, the double panel substrate 36 is provided and includes an upper rectangular panel 68 and a lower rectangular panel 70. Preferably, the panels may be made of a relatively stiff paperboard, but they could be made of any suitable material. The upper panel includes an opening or hole 72 sized to fit over the cover and ribs, as shown in FIGS. 1 to 3. The lower panel 70 includes a hole or opening 74 of a size slightly smaller than the hole 72 and about equal to the inside dimension of the upstanding wall 44 of the base 32. When bringing the panels 68 and 70 together in relation to the carrier, the panels are suitably adhesively or otherwise attached to each other adjacent to the outer edges and the flange 46 of the carrier base 32 is suitably attached such as by adhesive to the lower panel 70 to prevent the base from rotating. Thus, the cover flange 58 is free to rotate over the base flange to enable the cover to move between unlock and lock positions. Thus, the panels 68 and 70 are adhesively secured together at their edges or at least at the three free edges and the flange of the base 32 is adhesively secured to the lower panel 70 to prevent it from rotation relative to the double-panel retaining means 36.

While any suitable jig may be used to be removably connected to the orthodontic appliance, one form of jig, generally indicated by the numeral 76, is shown in FIGS. 15 to 17. This jig includes a central bracket engaging section or portion 78, opposite end sections 80 and 82, spaced apart downwardly projecting lugs 84 and 86, and tear-drop shaped protrusions or engaging areas 88 and 90. The end section 80 of this jig is longer than the end section 82 to offset the central bracket engaging section to accommodate a hooked bracket. The length of the jig is sized so that it will fit the carrier with the opposite ends bottoming in the seats 50 of the base and freely fit inside the upstanding wall of the cover. With respect to an orthodontic bracket, the jig is sized to fit between the tie wings of a standard edgewise twin-wing bracket, as shown in FIG. 14, and generally indicated by the numeral 92. This bracket includes a base 94 and upstanding therefrom tie wings 96 and 98. A layer of uncured adhesive 95 is provided on the base. Each tie wing includes upper and lower tie-wing tips and an outwardly opening archwire slot 100 is formed in both tie wings in the usual manner. The tie wings are mesiodistally spaced apart and define therebetween an occlusogingivally extending opening 102 into which the jig is removably inserted. Each tie-wing tip includes a labiolingually extending section and an occlusogingivally extending section, and the jig is designed so that the nodes or enlarged elements 88 and 90 will engage generally between the labiolingual sections of the tie wings to connect the jig to the bracket. It will be understood that the bracket may be for various prescriptions and have various built-in torque and tip values. The jigs are made of a softer material than the brackets and preferably of a suitable plastic so that when the jig is assembled or connected with the bracket, it will be frictionally held in place to removably connect the jig to the bracket. The central section 78 is also somewhat enlarged so that it can be grasped with a tweezers or suitable instrument, as seen in FIGS. 1 and

23, in order to manipulate the jigged appliance and to insert it into and withdraw it from the carrier as well as to mount the bracket onto a tooth. The jig also enhances the alignment of the bracket to the long axis of the tooth. Further, the jig may be provided with means for spacing the bracket a predetermined distance from the occlusal surface of a tooth.

While it is preferable and usual that the jig be aligned with the occlusogingival axis of the bracket, it should be appreciated that it could be aligned with the labiolingual axis if so desired. The jig may be suitably molded of a suitable plastic such as polyethylene or polystyrene and having a pliability or flexibility such as to enable it to easily be frictionally engageable with a bracket.

Although the carrier of the invention is shown to be used with a jigged edgewise twin-wing bracket, it can be appreciated that any type of bracket may be jigged to be placed in the carrier and that a jig would be structured to removably engage such a bracket or appliance. With respect to a prepasted buccal tube, the jig would be normally aligned with the mesiodistal axis of the tube, although the jig could be made to be aligned with the occlusogingival axis of a tube.

For shipment and storage of a prepasted bracket on a carrier, it is enclosed in a suitable bag, such as the bag 103 shown in FIG. 3. The bag would be of a suitable material to prevent curing of the uncured adhesive on the bracket, as previously mentioned. With respect to application of a light-cure adhesive on the base, the bag would be opaque to actinic radiation that would cure the adhesive, as described in U.S. Pat. No. 6,834,761.

A modified jig is shown in FIG. 19 and generally indicated by the numeral 76A. This jig may be considered to be a universal jig for use on many different types of brackets. It includes a central portion 104 for engagement with an instrument for manipulating the jig and a bracket or other appliance connected thereto. Opposing ends 106 and 108 and downwardly projecting lugs 110 and 112 extend from the central portion. The lugs are formed for attachment to a bracket or a tube in a suitable manner. The lugs are hook-shaped and facing each other for engagement of the tie-wing tips of single or multiple tie-wing brackets, as well as self-ligating and Tip Edge brackets. Tip-Edge is a trademark owned by TP Orthodontics, Inc.

It will be appreciated that a plurality of carriers may be maintained together on an elongated dual panel substrate 114, as shown in FIG. 18, to ship a bracket system to a user where the brackets are designed for specific teeth of a patient. In this embodiment, two rows of carriers 116 are shown with each row having five carriers for including up to a total of ten jigged brackets. Any number of jigged brackets may be shipped on this panel with the carriers, and it should also be appreciated that a panel having a greater or lesser number of carriers may be provided. The number of carriers may be such as to accommodate an entire bracket system of a desired prescription.

Another carrier embodiment of the invention is shown in FIGS. 20 to 22 and is generally indicated by the numeral 118. This carrier includes an upstanding generally cylindrical wall 120 having an annular flange 122 at the lower end for anchoring the carrier to a substrate. The inner side of the upstanding wall 120 includes an annular recess or detent 124, as particularly seen in FIGS. 20 and 22, to receive in snap-fit relation the opposite ends of a jig having a bracket connected thereto, as shown in the drawings. While the indent or recess is shown to be continuous and is in parallel relation to the upper end of the carrier, it should be appreciated that it would merely constitute opposing indents sized to engage the opposite ends of a bracket jig. In this embodiment, the walls would have sufficient flexibility to allow the jigged bracket to be snapped into place, as shown in FIGS. 21 and 22, and the relationship between the length of the jig and the depth of the indents or annular indent, would be such as to insure there would be a releasable engagement between the jig and the wall. In this instance, the upstanding wall would have sufficient flexibility to permit the jig to snap into place. It may be also appreciated that the flange 122 may be suitably secured to a substrate having an opening therethrough in alignment with the opening extending through the carrier. While the upstanding wall is shown to be ring-shaped or circular in form, it may be appreciated that the opposing walls could be flat or straight where the outer configuration of the carrier looking down on the carrier would be square or rectangular in shape. After mounting a jigged appliance on the carrier, it would be suitably encapsulated in a bag for handling and shipment.

Although the carrier embodiment of FIGS. 1 to 13 includes ring-shaped or circular shaped base and cover members, it will be appreciated that other geometrically shaped base and cover members for a carrier that include a sliding engagement between the cover and the base for locking and unlocking a jigged bracket to the carrier are within the scope of the invention. For example, a base having segmented arcuately formed areas that slidingly engage similar segmented arcuately formed areas of a cover can provide a locking and unlocking mode. In such an embodiment seats are employed for receiving the ends of a jig having a bracket removably connected thereto and a rim on the cover is provided over the top of the base to open or close the seats for unlocking and locking of the jigged bracket to the carrier. The invention further contemplates the provision of flat engaging members, as seen in the embodiment of FIGS. 23 to 27. Again, a sliding action or engagement between a fixed base and a sliding cover allows the opening of seats for a jigged bracket to be inserted or withdrawn and the closing of the seats to lock a jigged bracket to the carrier.

Referring now to the embodiment of FIGS. 23 to 27, the carrier is generally indicated by the numeral 126 and includes a base 128 and a cover 130. The base includes a generally rectangular upstanding wall having opposed parallel walls 132 and 134 connected by opposed parallel walls 136 and 138. Upwardly opening seats or slots 140 are provided in the walls 136 and 138 for receiving the ends of a jig having a bracket removably connected thereto. The lower ends of the walls 136 and 138 include flanges 141 that would be fixed in place so that the cover can slide on the base. Similarly, the cover 130 includes opposed walls 142 and opposed walls 143 that are upstanding and have formed along their upper ends a lip 144 having opposed slots 145. Flanges 146 are provided at the bottom ends of the opposed walls 142 and which ride on the flanges 141 of the base. The cover is also sized to be larger than the base but which has a width slightly larger to mate with the width of the base and a length large enough to allow the opening slots 145 to be aligned with the seats 140, as shown in FIG. 25, to allow insertion and withdrawal of a jigged bracket on the carrier. After slidably moving the cover relative to the base to cause the overhanging lip 144 to enclose the seats, the ends of the jig are locked in place on the seats. A dual panel substrate like that shown in FIGS. 1 and 6 would also be provided with an opening on the top panel such as to overlie the flanges of the cover and allow sliding movement of the cover between lock and unlock positions and an opening on the bottom panel to mate with the opening in the base. The flanges of the base would be suitably permanently connected such as by adhesive or the like to the bottom panel of the connecting panels, while the flange of the cover would be free to move between the panels. Similarly, the two panels would be adhesively connected adjacent to their edges to secure them together and secure the cover in position on the base.

The method of the invention involves supporting an orthodontic bracket on a carrier wherein the bracket includes a base having uncured adhesive thereon. A suitable jig is removably connected to the bracket to define a jigged bracket that can be manipulated by an instrument for mounting in the carrier of the invention. The jig is elongated to extend beyond the gingival and occlusal ends of the bracket. The carrier of the invention includes a base having an upper edge with upwardly opening U-shaped seats on which the opposite ends of the jig will be received. A carrier is telescopically and slidably related to the base and includes a lip overlying the upper edge of the base such as to be able to cover the seats when the cover is slidably moved on the base. Opposed slots are formed in the lip capable of aligning with the seats to open the seats so that a jigged bracket may be inserted or withdrawn therefrom. After the jigged bracket is placed onto the carrier, the cover is slidably moved in order to bring the lip over the seats and lock the jigged appliance in place. A suitable means such as a dual panel substrate coacts with flanges on the cover and base in order to maintain them in slidable relationship with each other. The base is suitably connected to one of the panels, while the flange of the cover is free to be in slidable engagement with the flange of the base. Following the locking of a jigged bracket on a carrier, the carrier is inserted into a bag of suitable material and hermetically sealed for shipment of the carrier with the jigged bracket.

It will be understood that modifications and variations may be effected without departing from the scope of the novel concepts of the present invention, but it is understood that this application is to be limited only by the scope of the appended claims.

The invention is hereby claimed as follows:

1. A carrier for a prepasted orthodontic jigged appliance removably mounted on a jig, wherein said appliance includes a base having an uncured layer of adhesive thereon, and said jig having means for removably connecting to said appliance and opposed ends extending from opposite sides of the appliance, said carrier comprising:
    a base of relatively rigid material including,
    an upstanding member having an upper edge, and
    opposed upwardly opening generally U-shaped seats along the upper edge of said upstanding member, said seats adapted to receive said opposed ends of said jig,
    a cover slidably received on said upstanding member and coacting with said upstanding member to selectively retain said jigged appliance on the carrier,
    said cover including a lip overlying the upper edge of the upstanding member and opposed slots for selective alignment with the opposed seats,
    whereby aligning said slots with said seats permits mounting and demounting of a jigged appliance on said base and sliding of the cover on the base to misalign the slots and seats locks the jigged appliance to said carrier.

2. The carrier of claim 1, wherein said carrier base includes an opening in alignment with said upstanding member.

3. The carrier of claim 1, which further includes means for maintaining the base in fixed position and said cover in slidable relation to the base.

4. The carrier of claim 1, which further comprises a bag for enclosing the carrier with a jigged appliance therein to shield the adhesive from actinic radiation.

5. The carrier of claim 1, wherein the jig is of a soft plastic to facilitate deformation to allow a friction fit with the appliance.

6. The carrier of claim 1, wherein the upstanding member and the cover include arcuately formed slidably engaging surfaces.

7. The carrier of claim 1, wherein the upstanding member and the cover include planar slidably engaging surfaces.

8. The carrier of claim 1, wherein the upstanding member and the cover are substantially cylindrically formed.

9. The carrier of claim 1, wherein the appliance is a twin wing edgewise bracket having a pair of tie wings spaced apart mesiodistally thereby defining an opening therebetween, and said jig having an intermediate section engaging in said opening such as to removably connect the jig and bracket together.

10. A method of supporting an orthodontic bracket on a carrier, wherein said bracket includes a base having uncured adhesive thereon, and occlusal and gingival ends between which is the occlusal-gingival height of said bracket, said method comprising the steps of:
    removably connecting a jig to the bracket to provide a jigged bracket,
    wherein the jig includes an elongated member of a length greater than the occlusal-gingival height of said bracket so that the opposite ends of the jig extend beyond the occlusal and gingival ends of the bracket, and
    mounting the jigged bracket on said carrier,
    wherein the carrier includes
    a base of relatively rigid material having,
    an upstanding member having an upper edge,
    opposed upwardly opening U-shaped seats at the upper edge of said upstanding member, said seats adapted to receive opposite ends of said jig,
    and a cover slidably received on said base and coacting with said upstanding member to retain said jigged bracket on the carrier,
    said cover including a lip overlying the upper edge of the upstanding member and opposed slots for selective alignment with the opposed seats,
    aligning said slots and seats,
    placing the jigged bracket on the carrier by causing opposite ends of the jig to pass through the slots and rest in said seats, and sliding said cover to cause the slots to be misaligned from said seats and the lip of said cover to overlie the ends of the jig and lock the jigged bracket to said carrier.

11. The method of claim 10, which further includes the step of maintaining the cover on the base, and the cover in slidable relation to the base.

12. The method of claim 10, wherein the step of mounting the jig on the bracket includes press-fitting the jig to the bracket.

13. The method of claim 6, wherein the upstanding member of the base is substantially arcuate in shape and the cover is substantially arcuate in shape.

14. The method of claim 6, wherein the upstanding member of the base is substantially arcuate in shape and the cover is substantially cylindrical in shape.

15. The method of claim 6, wherein the upstanding member of the base is substantially rectangular in shape and the cover is substantially rectangular in shape.

16. A carrier for a prepasted orthodontic appliance removably connected to a jig, wherein said appliance includes a base having an uncured layer of adhesive thereon, and said jig having means for removably connecting to said appliance and opposed ends extending from opposite sides of the appliance, said carrier comprising:
    an upstanding member having opposed side walls,
    means on the opposed side walls for removably receiving and holding the opposed ends of said jig on said upstanding member such that the appliance adhesive does not contact the upstanding member, said means on said opposed side walls including a sliding member on said upstanding member coacting therewith for selectively locking the opposed ends of the jig to the carrier, and a substrate on which the upstanding member is mounted.

17. The carrier of claim 16, which further includes a container encapsulating the carrier and preventing the curing of the adhesive.

18. The carrier of claim 16, wherein said upstanding member is cylindrically shaped.

19. The carrier of claim 16, wherein said means for receiving and holding the opposed ends of the jig include recess/indents in said side walls.

20. The carrier of claim 16, wherein said upstanding member includes a flange at one end that is attached to said substrate.

21. The carrier of claim 16, which further includes a bag encapsulating the carrier for preventing the adhesive from being exposed to light-curing energy.

22. The carrier of claim 16, wherein said upstanding member is rectangularly shaped.

* * * * *